(12) United States Patent
Reid, Jr.

(10) Patent No.: US 9,943,359 B2
(45) Date of Patent: Apr. 17, 2018

(54) LIMITED REUSE ABLATION NEEDLES AND ABLATION DEVICES FOR USE THEREWITH

(75) Inventor: William O. Reid, Jr., Longmont, CO (US)

(73) Assignee: Covidien LP, Mansfield, MA (US)

( * ) Notice: Subject to any disclaimer, the term of this patent is extended or adjusted under 35 U.S.C. 154(b) by 861 days.

(21) Appl. No.: 13/460,414

(22) Filed: Apr. 30, 2012

(65) Prior Publication Data
US 2013/0289559 A1  Oct. 31, 2013

(51) Int. Cl.
| | | |
|---|---|---|
| A61B 18/18 | (2006.01) | |
| A61B 18/14 | (2006.01) | |
| A61B 17/00 | (2006.01) | |
| A61B 18/00 | (2006.01) | |
| A61B 90/00 | (2016.01) | |

(52) U.S. Cl.
CPC ....... *A61B 18/1477* (2013.01); *A61B 2017/00867* (2013.01); *A61B 2018/00178* (2013.01); *A61B 2018/1425* (2013.01); *A61B 2090/0814* (2016.02)

(58) Field of Classification Search
CPC ......... A61B 18/00; A61B 18/18; A61B 17/00; A61B 2017/00004; A61B 2018/00172; A61B 2018/00178; A61B 2018/0091; A61B 2018/00916; A61B 2018/00922; A61B 2090/0814; A61B 2560/0266; A61B 2560/028; A61B 2560/0285;
(Continued)

(56) References Cited

U.S. PATENT DOCUMENTS

| | | |
|---|---|---|
| D223,367 S | 4/1972 | Kountz |
| D263,020 S | 2/1982 | Rau, III |
| (Continued) | | |

FOREIGN PATENT DOCUMENTS

| | | |
|---|---|---|
| CN | 1103807 A | 6/1995 |
| DE | 390937 C | 3/1924 |
| (Continued) | | |

OTHER PUBLICATIONS

European Search Report EP 06019768 dated Jan. 17, 2007.
(Continued)

*Primary Examiner* — Eric D. Bertram
*Assistant Examiner* — Elizabeth K So

(57) ABSTRACT

A surgical instrument includes a reusable component and a limited-use component. The reusable component includes a first electrical contact. The limited-use component is releasably engagable with the reusable component. The limited-use component includes a second electrical contact configured to electrically couple to the first electrical contact to establish electrical communication between the reusable component and the limited-use component. The second electrical contact is movable from a first position, wherein the second electrical contact is positioned to electrically couple to the first electrical contact upon engagement of the limited-use component and the reusable component to one another, to a second position, wherein the second electrical contact is positioned to inhibit electrical coupling to the first electrical contact upon engagement of the limited-use component and the reusable component to one another.

7 Claims, 7 Drawing Sheets

(58) Field of Classification Search
CPC .. A61B 1/00062; A61N 1/375; A61N 1/0472; A61N 1/048; A61N 1/0488
See application file for complete search history.

(56) References Cited

U.S. PATENT DOCUMENTS

| | | | |
|---|---|---|---|
| D266,842 S | 11/1982 | Villers et al. | |
| 4,359,052 A | 11/1982 | Staub | |
| D278,306 S | 4/1985 | McIntosh | |
| D295,893 S | 5/1988 | Sharkany et al. | |
| D295,894 S | 5/1988 | Sharkany et al. | |
| 4,911,161 A | 3/1990 | Schechter | |
| D354,218 S | 1/1995 | Van de Peer | |
| 5,383,874 A | 1/1995 | Jackson et al. | |
| 5,807,392 A | 9/1998 | Eggers | |
| D424,693 S | 5/2000 | Pruter | |
| D424,694 S | 5/2000 | Tetzlaff et al. | |
| D425,201 S | 5/2000 | Tetzlaff et al. | |
| 6,221,070 B1 | 4/2001 | Tu et al. | |
| D449,886 S | 10/2001 | Tetzlaff et al. | |
| D457,958 S | 5/2002 | Dycus et al. | |
| D457,959 S | 5/2002 | Tetzlaff et al. | |
| 6,464,689 B1 | 10/2002 | Qin et al. | |
| D487,039 S | 2/2004 | Webster et al. | |
| D496,997 S | 10/2004 | Dycus et al. | |
| D499,181 S | 11/2004 | Dycus et al. | |
| D525,361 S | 7/2006 | Hushka | |
| D531,311 S | 10/2006 | Guerra et al. | |
| D533,942 S | 12/2006 | Kerr et al. | |
| D535,027 S | 1/2007 | James et al. | |
| D541,418 S | 4/2007 | Schechter et al. | |
| D541,938 S | 5/2007 | Kerr et al. | |
| 7,300,436 B2 | 11/2007 | Penny et al. | |
| D564,662 S | 3/2008 | Moses et al. | |
| 7,367,973 B2 | 5/2008 | Manzo et al. | |
| D576,932 S | 9/2008 | Strehler | |
| 7,435,112 B1 | 10/2008 | Miller et al. | |
| D594,736 S | 6/2009 | Esjunin | |
| D594,737 S | 6/2009 | Kelly et al. | |
| D606,203 S | 12/2009 | Husheer et al. | |
| D613,412 S | 4/2010 | DeCarlo | |
| D634,010 S | 3/2011 | DeCarlo | |
| 8,998,938 B2 * | 4/2015 | Seto et al. | 606/167 |
| 2003/0199735 A1 * | 10/2003 | Dickopp | A61B 1/00062 600/104 |
| 2003/0208196 A1 | 11/2003 | Stone | |
| 2004/0110428 A1 * | 6/2004 | Desinger | A61B 18/12 439/894 |
| 2004/0172016 A1 | 9/2004 | Bek et al. | |
| 2004/0267254 A1 | 12/2004 | Manzo et al. | |
| 2006/0161054 A1 | 7/2006 | Reuss et al. | |
| 2009/0065565 A1 | 3/2009 | Cao | |
| 2011/0288543 A1 | 11/2011 | Cheng et al. | |
| 2012/0105136 A1 * | 5/2012 | Fausset | H01H 85/46 327/525 |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 4303882 A1 | 8/1994 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10224154 A1 | 12/2003 |
| DE | 10310765 A1 | 9/2004 |
| DE | 10328514 B3 | 3/2005 |
| DE | 102004022206 A1 | 12/2005 |
| DE | 202005015147 U1 | 2/2006 |
| EP | 0 246 350 A1 | 11/1987 |
| EP | 0 521 264 A2 | 1/1993 |
| EP | 0 556 705 A1 | 8/1993 |
| EP | 0 558 429 A1 | 9/1993 |
| EP | 0 648 515 A1 | 4/1995 |
| EP | 0 836 868 A2 | 4/1998 |
| EP | 0 882 955 A1 | 12/1998 |
| EP | 0979658 A1 | 2/2000 |
| EP | 1 159 926 A2 | 12/2001 |
| EP | 1829495 A1 | 9/2007 |
| EP | 2322077 A1 | 5/2011 |
| EP | 2653126 A1 | 10/2013 |
| FR | 179 607 | 11/1906 |
| FR | 1 275 415 A | 11/1961 |
| FR | 1 347 865 A | 1/1964 |
| FR | 2 235 669 A1 | 1/1975 |
| FR | 2 276 027 A1 | 1/1976 |
| FR | 2 313 708 A1 | 12/1976 |
| FR | 2 502 935 A1 | 10/1982 |
| FR | 2 517 953 A1 | 6/1983 |
| FR | 2 573 301 A1 | 5/1986 |
| FR | 2 862 813 A1 | 5/2005 |
| FR | 2 864 439 A1 | 7/2005 |
| JP | 5-5106 | 1/1993 |
| JP | 05-40112 | 2/1993 |
| JP | 06343644 A | 12/1994 |
| JP | 07265328 A | 10/1995 |
| JP | 08056955 A | 3/1996 |
| JP | 08252263 A | 10/1996 |
| JP | 09000492 A | 1/1997 |
| JP | 09010223 A | 1/1997 |
| JP | 11244298 A | 9/1999 |
| JP | 2000342599 A | 12/2000 |
| JP | 2000350732 A | 12/2000 |
| JP | 2001003776 A | 1/2001 |
| JP | 2001008944 A | 1/2001 |
| JP | 2001029356 A | 2/2001 |
| JP | 2001037775 A | 2/2001 |
| JP | 2001128990 A | 5/2001 |
| JP | 2001231870 A | 8/2001 |
| JP | 2008142467 A | 6/2008 |
| SU | 166452 | 11/1964 |
| SU | 401367 A1 | 10/1973 |
| SU | 727201 A2 | 4/1980 |
| WO | 97/24073 | 7/1997 |
| WO | 2004/096032 A1 | 11/2004 |
| WO | 2010/035831 A1 | 4/2010 |

OTHER PUBLICATIONS

European Search Report EP 06020574.7 dated Oct. 2, 2007.
European Search Report EP 06020583.8 dated Feb. 7, 2007.
European Search Report EP 06020584.6 dated Feb. 1, 2007.

(56) References Cited

OTHER PUBLICATIONS

European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2008.
European Search Report EP 07015601.3 dated Jan. 4, 2008.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001016.8 dated Jan. 4, 2008.
European Search Report EP 08001019 dated Sep. 23, 2008.
European Search Report EP 08004974.5 dated Apr. 6, 2011.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08007924.7 partial dated Aug. 17, 2010.
European Search Report EP 08011282 dated Aug. 14, 2009.
European Search Report EP 08011705 dated Aug. 20, 2009.
European Search Report EP 08011705.4 extended dated Nov. 4, 2009.
International Search Report PCT/US98/18640 dated Jan. 29, 1999.
International Search Report PCT/US98/23950 dated Jan. 14, 1999.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2005.
International Search Report PCT/US05/36168 dated Aug. 28, 2006.
International Search Report PCT/US08/052460 dated Apr. 24, 2008.
International Search Report PCT/US09/31658 dated Mar. 11, 2009.
International Search Report PCT/US10/032796 dated Jul. 28, 2010.

U.S. Appl. No. 12/861,333, filed Aug. 23, 2010, Joseph D. Brannan.
U.S. Appl. No. 12/944,951, filed Nov. 12, 2010, Joseph D. Brannan.
U.S. Appl. No. 12/977,390, filed Dec. 23, 2010, Joseph D. Brannan.
U.S. Appl. No. 12/977,415, filed Dec. 23, 2010, Joseph D. Brannan.
U.S. Appl. No. 12/985,124, filed Jan. 5, 2011, Joseph D. Brannan.
U.S. Appl. No. 12/985,136, filed Jan. 5, 2011, Joseph D. Brannan.
U.S. Appl. No. 12/985,155, filed Jan. 5, 2011, Joseph D. Brannan.
U.S. Appl. No. 12/985,179, filed Jan. 5, 2011, Joseph D. Brannan.
U.S. Appl. No. 13/020,562, filed Feb. 3, 2011, Joseph D. Brannan.
U.S. Appl. No. 13/020,664, filed Feb. 3, 2011, Kenlyn S. Bonn.
U.S. Appl. No. 13/024,041, filed Feb. 9, 2011, Joseph D. Brannan.
U.S. Appl. No. 13/029,521, filed Feb. 17, 2011, Joseph D. Brannan.
U.S. Appl. No. 13/029,594, filed Feb. 17, 2011, Joseph D. Brannan.
U.S. Appl. No. 13/043,665, filed Mar. 9, 2011, Richard A. Willyard.
U.S. Appl. No. 13/043,694, filed Mar. 9, 2011, Richard A. Willyard.
U.S. Appl. No. 13/050,729, filed Mar. 17, 2011, Casey M. Ladtkow.
U.S. Appl. No. 13/083,185, filed Apr. 8, 2011, Arnold V. Decarlo.
U.S. Appl. No. 13/083,256, filed Apr. 8, 2011, Joseph D. Brannan.
U.S. Appl. No. 13/113,736, filed May 23, 2011, Ladtkow et al.
U.S. Appl. No. 13/118,929, filed May 31, 2011, Bonn et al.
U.S. Appl. No. 13/206,075, filed Aug. 9, 2011, Lee et al.
U.S. Appl. No. 13/236,997, filed Sep. 20, 2011, Behnke II, et al.
U.S. Appl. No. 13/237,068, filed Sep. 20, 2011, Behnke II, et al.
U.S. Appl. No. 13/237,187, filed Sep. 20, 2011, Behnke II, et al.
U.S. Appl. No. 13/237,342, filed Sep. 20, 2011, Behnke II, et al.
U.S. Appl. No. 13/237,488, filed Sep. 20, 2011, Behnke II, et al.
U.S. Appl. No. 13/267,369, filed Oct. 6, 2011, Prakash et al.
U.S. Appl. No. 13/268,143, filed Oct. 7, 2011, Kenlyn S. Bonn.
U.S. Appl. No. 13/281,605, filed Oct. 26, 2011, Prakash et al.
U.S. Appl. No. 13/290,462, filed Nov. 7, 2011, Kenlyn S. Bonn.
U.S. Appl. No. 13/298,461, filed Nov. 17, 2011, Buysse et al.
U.S. Appl. No. 13/344,753, filed Jan. 6, 2012, Lee et al.
U.S. Appl. No. 13/343,788, filed Jan. 5, 2012, William O. Reid, Jr.
U.S. Appl. No. 13/343,798, filed Jan. 5, 2012, William O. Reid, Jr.
U.S. Appl. No. 13/344,790, filed Jan. 6, 2012, Lee et al.
U.S. Appl. No. 13/351,463, filed Jan. 17, 2012, Smith et al.
U.S. Appl. No. 13/351,553, filed Jan. 17, 2012, Mahajan et al.
U.S. Appl. No. 13/358,129, filed Jan. 25, 2012, Joseph D. Brannan.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08020530.5 dated May 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09012389.4 dated Jul. 6, 2010.
European Search Report EP 09151621 dated Jun. 18, 2009.
European Search Report EP 09156861.8 dated Aug. 4, 2009.
European Search Report EP 09161502.1 dated Sep. 2, 2009.
European Search Report EP 09161502.1 extended dated Oct. 30, 2009.
European Search Report EP 09165976.3 extended dated Mar. 17, 2010.
European Search Report EP 09166708 dated Oct. 15, 2009.
European Search Report EP 09166708.9 dated Mar. 18, 2010.
European Search Report EP 09169376.2 extended dated Dec. 16, 2009.
European Search Report EP 09172188.6 extended dated Apr. 23, 2010.
European Search Report EP 09172838.6 extended dated Jan. 20, 2010.
European Search Report EP 09173268.5 extended dated Jan. 27, 2010.
European Search Report EP 09704429.1 extended dated Mar. 23, 2011.
European Search Report EP 10001767.2 extended dated Jun. 18, 2010.
European Search Report EP 10004950.1 extended dated Jul. 2, 2010.
European Search Report EP 10004951.9 extended dated Jul. 2, 2010.

(56) References Cited

OTHER PUBLICATIONS

European Search Report EP 10005533.4 extended dated Sep. 24, 2010.
European Search Report EP 10005534.2 extended dated Sep. 17, 2010.
European Search Report EP 10006373.4 extended dated Nov. 11, 2010.
European Search Report EP 10008139.7 extended dated Nov. 30, 2010.
European Search Report EP 10008140.5 extended dated Dec. 28, 2010.
European Search Report EP 10008533.1 extended dated Dec. 20, 2010.
European Search Report EP 10008850.9 extended dated Nov. 30, 2010.
European Search Report EP 10009731.0 extended dated Jan. 28, 2011.
European Search Report EP 10009732.8 extended dated Jan. 26, 2011.
European Search Report EP 10010943.8 extended dated Feb. 1, 2011.
European Search Report EP 10011750.6 extended dated Feb. 1, 2011.
European Search Report EP 10014042.5 extended dated Feb. 18, 2011.
European Search Report EP 10014080.5 extended dated Mar. 17, 2011.
European Search Report EP 10014081.3 extended dated Mar. 17, 2011.
European Search Report EP 10014705.7 extended dated Apr. 27, 2011.
European Search Report EP 10158944.8 extended dated Jun. 21, 2010.
European Search Report EP 10161596.1 extended dated Jul. 28, 2010.
European Search Report EP 10161722.3 extended dated Jun. 16, 2010.
European Search Report EP 10163235.4 dated Aug. 10, 2010.
European Search Report EP 10172634.7 dated Nov. 9, 2010.
European Search Report EP 10185413.1 dated Dec. 7, 2010.
European Search Report EP 10185413.1 dated Mar. 14, 2011.
European Search Report EP 10191321.8 dated Apr. 7, 2011.
European Search Report EP 11000548.5 extended dated Apr. 14, 2011.
European Search Report EP 11004942 dated Sep. 23, 2011.
European Search Report EP 11174318.3 dated Nov. 7, 2011.
International Search Report PCT/US97/05066 dated Jun. 24, 1997.
European Search Report EP 02786604.5 dated Feb. 10, 2010.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Aug. 4, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
Koyle et al., "Laparoscopic Palomo Varicocele Ligation in Children and Adolescents" Pediatric Endosurgery & Innovative Techniques, vol. 6, No. 1, 2002.
LigaSureTM Vessel Sealing System, the Seal of Confidence in General , Gynecologic, Urologic, and Laparoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSureTM Vessel Sealing System and LigaSureTM Atlas 20 cm Open Instrument" Innovations That Work, Jun. 2003.
Muller et al., "Extended Left Hemicolectomy Using the LigaSureTM Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences-Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.

(56) References Cited

OTHER PUBLICATIONS

Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSureTM versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSureTM Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817-825.
Urologix, Inc.—Medical Professionals: TargisTM Technology (Date Unknown). "Overcoming the Challenge" located at: <http://www.urologix.com!medicaUtechnology.html > Nov. 18, 1999; 3 pages.
Urrutia et al., (1988). "Retractable-Barb Needle for Breast Lesion Localization: Use in 60 Cases," Radiology 169 (3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.

Vallfors et al., "Automatically Controlled Bipolar Electrocoagulation—'COA-COMP'" Neurosurgical Review 7:2-3 (1984) pp. 187-190.
W. Scott Helton, "LigaSureTM Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Search Report EP 98300964.8 dated Dec. 13, 2000.
European Search Report EP 98944778 dated Nov. 7, 2000.
European Search Report EP 98958575.7 dated Oct. 29, 2002.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion NeedlelWire Localizer, Namic ® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSureTM Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSureTM Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.

(56) References Cited

OTHER PUBLICATIONS

Chou, C.K., (1995) "Radiofrequency Hyperthermia in Cancer Therapy," Chapter 94 In Biologic Effects of Nonionizing Electromagnetic Fields, CRC Press, Inc., pp. 1424-1428.
Chung et al., "Clinical Experience of Sutureless Closed Hemorrhoidectomy with LigaSureTM" Diseases of the Colon & Rectum, vol. 46, No. 1, Jan. 2003.
Cosman et al., "Methods of Making Nervous System Lesions" in William RH, Rengachary SS (eds): Neurosurgery, New York: McGraw-Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15: (1984), pp. 945-950.
Crawford et al., "Use of the LigaSureTM Vessel Sealing System in Urologic Cancer Surger" Grand Rounds in Urology 1999, vol. 1, Issue 4, pp. I 0-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/ Product Literature 2000.
Esterline, "Light Key Projection Keyboard", Advanced Input Systems, <http://www.advanced-input.com/lightkey> (2002).
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. Of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSureTM Vessel Sealing System: A Case Report" Innovations That Work, Feb. 2002.
Humphries Jr. et al., "Finite-Element Codes to Model Electrical Heating and Non-Llnear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSureTM Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSureTM Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol., BME-31, No. 1, Jan. 1984, pp. 28-37.
Johnson, "Use of the LigaSureTM Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, " LigaSureTM System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Extended European Search report issued in corresponding application No. EP13785161.4 on Oct. 29, 2015.
Chinese Office Action issued in corresponding application No. 201380022429.4 on May 26, 2016.
Chinese Office Action issued in corresponding application No. 2015-510254 on Sep. 14, 2016.
International Search Report PCT/US2013/028541 mailed Jun. 21, 2013.
Examination Report for corresponding Australian Application No. 2013257269 dated Nov. 18, 2016.
Japanese Office Action issued in corresponding application No. 2015-510254 dated Sep. 14, 2016.
Extended European Search Report issued in Appl. No. EP 16197560.2 dated Jun. 2, 2017.
European Search Report EP 13164267 dated Aug. 21, 2013.

\* cited by examiner

LIMITED REUSE ABLATION NEEDLES AND ABLATION DEVICES FOR USE THEREWITH

BACKGROUND

Technical Field

The present disclosure relates to surgical instruments and, more particularly, to ablation devices including disposable needles configured for single-use or a limited amount and/or number of uses.

Background of Related Art

Energy-based tissue treatment is well known in the art. Various types of energy (e.g., electrosurgical, ultrasonic, microwave, cryogenic, thermal, laser, etc.) are applied to tissue to achieve a desired result, e.g., to cut, ablate, coagulate, and/or seal tissue.

Electrosurgery involves the application of radio frequency (RF) energy to a surgical site to cut, ablate, coagulate, and/or seal tissue. In monopolar electrosurgery, a source or active electrode, which is typically part of the surgical instrument held by the surgeon, delivers RF electrical current from a generator to tissue, while a patient return electrode is placed remotely from the active electrode to carry the current back to the generator.

In tissue ablation electrosurgery, for example, the RF energy may be delivered to targeted tissue by a probe or needle. More specifically, in use, the needle is typically advanced through tissue to a desired position either prior to or during application of energy to tissue. After repeated use, these needles may become dull, bent, or otherwise deformed and, consequently, may become more difficult to place and operate upon subsequent use. As such, ablation devices have been developed which include replaceable needles, thus allowing the needle to be replaced after one or more uses without requiring replacement of the entire device (e.g., the handpiece).

SUMMARY

As used herein, the term "distal" refers to the portion that is being described which is further from a user, while the term "proximal" refers to the portion that is being described which is closer to a user. Further, to the extent consistent with one another, any of the aspects described herein may be used in conjunction with any of the other aspects described herein.

In accordance with aspects of the present disclosure, a surgical instrument is provided generally including a reusable component and a limited-use component. The reusable a component includes a first electrical contact. The limited-use component is releasably engagable with the reusable component and includes a second electrical contact configured to electrically couple to the first electrical contact to establish electrical communication between the reusable component and the limited-use component. The second electrical contact is movable from a first position, wherein the second electrical contact is positioned to electrically couple to the first electrical contact upon engagement of the limited-use component and the reusable component to one another, to a second position, wherein the second electrical contact is positioned to inhibit electrical coupling to the first electrical contact upon engagement of the limited-use component and the reusable component to one another.

In one aspect, the surgical instrument includes an ablation device having a reusable handle assembly and a limited-use needle electrode assembly releasably engagable with the handle assembly. In such aspects, in the first position, the second electrical contact may be disposed at a proximal end of the limited-use needle electrode assembly to facilitate engagement to the first electrical contact of the reusable handle assembly. In the second position, on the other hand, the second electrical contact may be retracted into the limited-use needle electrode assembly to inhibit electrical coupling to the first electrical contact.

In another aspect, the second electrical contact is coupled to a biasing member and is supported via a support member. In such aspects, the support member is configured to transition from a first condition, wherein the support member retains the second electrical contact in the first position against the bias of the biasing member, and a second condition, wherein the support member no longer supports the second electrical contact, thereby permitting the second electrical contact to move to the second position under the bias of the biasing member.

In yet another aspect, the support member is transitioned from the first condition to the second condition upon application of a fluid thereto, heating to a pre-determined temperature, application of electrical energy thereto, and/or application of chemicals thereto.

In still another aspect, the support member is formed from a dissolvable material, a phase-change material, or a collapsible scaffold.

In yet another aspect, the second electrical contact is supported by a retention element. The retention element is transitionable from a first condition, wherein the retention element retains the second electrical contact in the first position, and a second condition, wherein the retention element effects movement of the second electrical contact to the second position.

In still yet another aspect, the retention element is transitioned from the first condition to the second condition upon application of a fluid thereto, heating to a pre-determined temperature, application of electrical energy thereto, and/or application of chemicals thereto.

In another aspect, electrical communication between the first and second electrical contacts is configured for transmitting electrical energy to the reusable component and/or identifying the reusable component.

Another surgical instrument provided in accordance with aspects of the present disclosure generally includes a reusable component including a first electrical contact and a limited-use component releasably engagable with the reusable component. The limited-use component includes a second electrical contact configured to electrically couple to the first electrical contact to establish electrical communication between the reusable component and the limited-use component. The second electrical contact is movable from a first position, wherein mechanical engagement of the reusable component and the limited-use component is permitted, to a second position, wherein the second electrical contact inhibits mechanical engagement of the reusable component and the limited-use component to one another.

In one aspect, the surgical instrument includes an ablation device having a reusable handle assembly and a limited-use needle electrode assembly releasably engagable with the handle assembly.

In another aspect, the first electrical contact includes a first pin and the second electrical contact includes a second pin. In the first position, the second pin is positioned to permit insertion of the first pin at least partially into the limited-use component to permit mechanical engagement of the reusable component and the limited-use component to one another. In the second position, the second pin is positioned to inhibit insertion of the first pin into the limited-use component, thereby inhibiting mechanical engagement of the reusable component and the limited-use component to one another.

In another aspect, the second electrical contact is transitioned from the first position to the second position upon heating to a pre-determined temperature. Further, the second electrical contact may be formed partially (or entirely) from a ferromagnetic material or a shape-memory material.

In yet another aspect, electrical communication between the first and second electrical contacts is configured for transmitting electrical energy to the reusable component and/or identifying the reusable component.

A surgical instrument provided in accordance with aspects of the present disclosure includes a reusable component including a first electrical contact and a limited-use component releasably engagable with the reusable component. The limited-use component includes a second electrical contact that is configured to electrically couple to the first electrical contact to establish electrical communication between the reusable component and the limited-use component. The second electrical contact is incorporated within a self-destructible cell that is configured for transitioning between an operable condition, wherein electrical communication is established between the first and second electrical contacts upon coupling of the first and second electrical contacts to one another, and a destroyed condition, wherein electrical communication between the first and second electrical contacts is inhibited.

In one aspect, the second electrical contact is incorporated into a galvanic cell that is configured to corrode to inhibit electrical communication between the first and second electrical contacts.

In another aspect, electrical communication between the first and second electrical contacts is configured for transmitting electrical energy to the reusable component and/or identifying the reusable component.

BRIEF DESCRIPTION OF THE DRAWINGS

Various aspects of the present disclosure are described herein with reference to the drawings wherein like reference numerals identify similar or identical elements.

DETAILED DESCRIPTION

Figure 1:
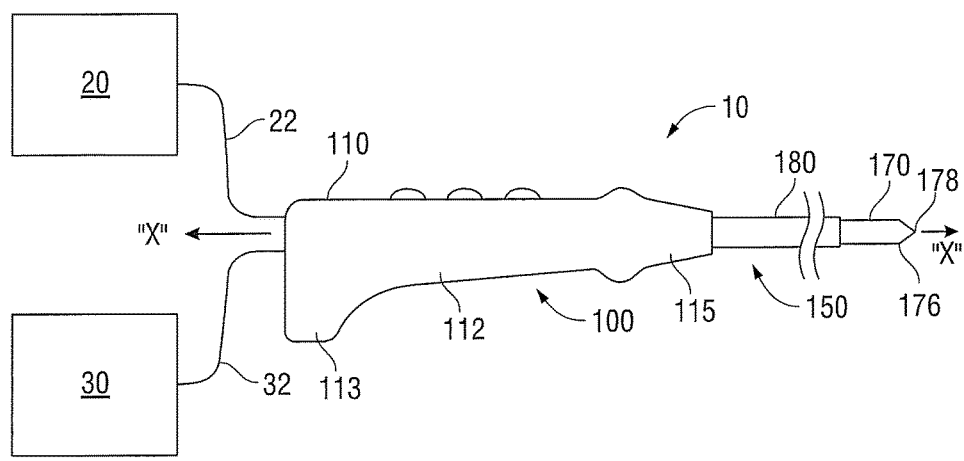
FIG. 1 is a side view of an electrosurgical ablation system provided in accordance with the present disclosure.
Figure 2:
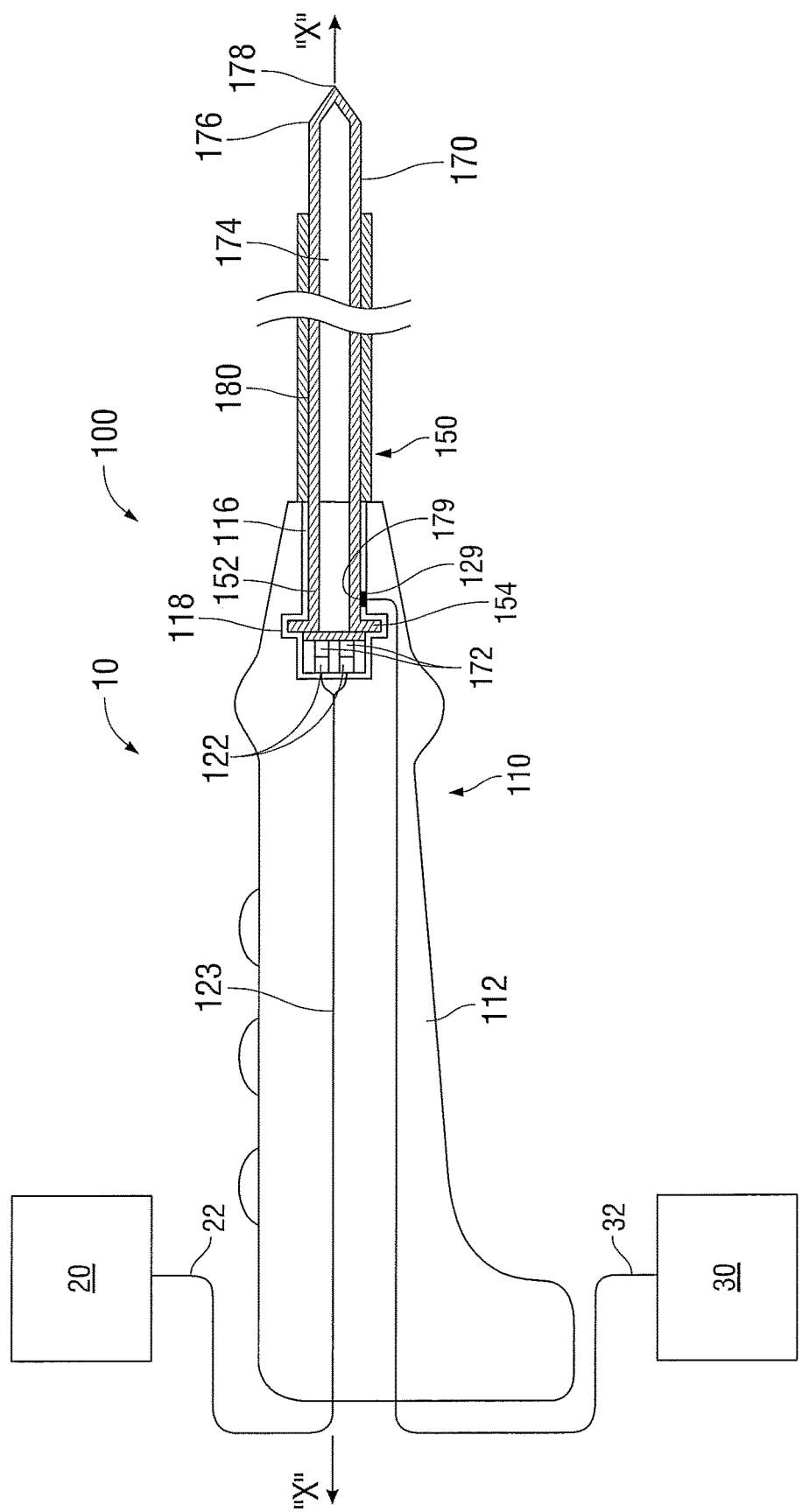
FIG. 2 is a longitudinal, cross-sectional view of the electrosurgical ablation system of FIG. 1.

Referring initially to FIGS. 1-2, an ablation system provided in accordance with the present disclosure is shown generally designated by reference numeral 10. Although ablation system 10 is shown configured as an RF-ablation system 10, the present disclosure is equally applicable for use with microwave ablation systems, or any other suitable surgical system including single-use or limited-use disposable components. Obviously, different considerations apply depending on the particular device and/or system used; however, the novel aspects with respect to inhibiting or limiting re-use of the needle (or other component) remains generally consistent regardless of the particular type of device and/or system used. For the purposes herein, ablation system 10 is generally described.

Continuing with reference to FIGS. 1-2, ablation device 100 of ablation system 10 generally includes a handle assembly 110 and a needle electrode assembly 150 releasably engagable with and extending from handle assembly 110. Although only one needle electrode assembly 150 is shown, additional needle electrode assemblies, either similar to or different from needle electrode assembly 150, may be provided for releasable engagement with handle assembly 110. As such, a desired needle electrode assembly may be selected and engaged to handle assembly 110, depending on a particular purpose and/or to replace a "spent" needle, e.g., a used needle, in the case of single-use needles, or a needle that has reached its usage limit and/or its maximum number of uses, in the case of limited use needles.

Handle assembly 110 includes a housing 112 which may be ergonomically or otherwise configured to facilitate the grasping and manipulation of housing 112 by a user to position needle electrode assembly 150 as desired. Housing 112 is formed from an insulative material and defines proximal and distal ends 113, 115, respectively. Proximal end 113 of housing is configured to receive lines 22, 32 from an energy source, e.g., generator 20, and cooling fluid source 30, respectively, for supplying energy and cooling fluid, respectively, to needle electrode assembly 150. Distal end 115 of housing 112 defines an engagement recess 116 configured to receive proximal end 152 of needle electrode assembly 150 therein for engaging needle electrode assembly 150 and handle assembly 110 to one another. More specifically, engagement recess 116 of housing 112 defines one or more notches 118 therein that are configured to engage protrusions 154 extending outwardly from proximal end 152 of needle electrode assembly 150 upon insertion of needle electrode assembly 150 into engagement recess 116 of housing 112 for releasably mechanically engaging needle electrode assembly 150 and handle assembly 110 to one another. Other releasable engagement mechanisms, e.g., snap-fit engagements, threaded-engagements, friction-fit engagements, etc., are also contemplated.

With continued reference to FIGS. 1-2, handle assembly 110 further includes a pair of electrical contacts 122 (although greater or fewer contacts are also contemplated) disposed on the base surface of engagement recess 116 that are configured to electrically couple to corresponding electrical contacts 172 positioned at proximal end 152 of needle electrode assembly 150 upon mechanical engagement of handle assembly 110 and needle electrode assembly 150 to one another, thereby establishing electrical communication between handle assembly 110 and needle electrode assembly 150 upon mechanical engagement of handle assembly 110 and needle electrode assembly 150 to one another. One or more wires 123 extending through housing 112 of handle assembly 110 couple contacts 122 to line 22, which extends proximally from housing 112 of handle assembly 110, ultimately coupling to generator 20. As such, power and/or control signals may be transmitted between generator 20 and needle electrode assembly 150 via the pairs of electrically-coupled contacts 122, 172. In particular, contacts 122, 172 may be configured for establishing a conductive path for transmission of energy between generator 20 and needle electrode assembly 150. As such, upon activation, energy can be transmitted from generator 20 to needle electrode assembly 150, e.g., via line 22, wires 123, and contacts 122, 172, and, ultimately, conducted through tissue to ablate or otherwise treat tissue. As an alternative to external generator 20, it is contemplated that generator 20 be incorporated into handle assembly 110, thus providing a hand-held ablation device 100.

One of the pairs of contacts 122, 172 may be utilized for identifying or verifying the identification of the particular type of needle electrode assembly 150 engaged with handle assembly 110. This feature helps ensure that an acceptable needle electrode assembly 150 has been engaged to handle assembly 110 and/or that the proper energy delivery and control parameters for the particular needle electrode assembly 150 engaged with handle assembly 110 are provided by generator 20. Additionally or alternatively, the same or a different pair of contacts 122, 172 may be utilized to indicate the number of times that the particular needle electrode assembly 150 engaged with handle assembly 110 has been used. Further, the operation of cooling fluid source 30 may also be at least partially dependent upon the particular type of needle electrode assembly 150 detected. Thus, identifying information for the particular type of needle electrode assembly 150 engaged to handle assembly 110 may be relayed to and utilized by cooling fluid source 30 for controlling the supply of cooling fluid to needle electrode assembly 150 in accordance therewith. Other configurations of contact(s) or similar features for establishing electrical communication and electrical energy transmission between handle assembly 110 and needle electrode assembly 150 are also contemplated.

Needle electrode assembly 150 defines a longitudinal axis "X-X" and includes an electrically-conductive needle 170 defining a hollow interior 174, an insulative sleeve 180 (or coating) disposed about a portion of the external surface of needle 170, and, as mentioned above, one or more electrical contacts 172 configured to permit electrical coupling of needle 170 to handle assembly 110 upon mechanical engagement of needle electrode assembly 150 and handle assembly 110 to one another.

Proximal end 152 of needle electrode assembly 150 is configured for insertion into engagement recess 116 of housing 112 of handle assembly 110 and includes a pair of outwardly-extending protrusions 154 (or other suitable complementary structure) configured to releasably engage notches 118 defined within engagement recess 116 of handle assembly 110 to releasably engage needle electrode assembly 150 within engagement recess 116 of handle assembly 110.

Continuing with reference to FIGS. 1-2, needle 170 extends distally from engagement recess 116 of housing 112 of handle assembly 110 to distal end 176 thereof, which defines a distal tip 178 configured to facilitate the penetration of tissue while minimizing the risk of hemorrhage from the puncture tract, although other distal tip configurations are also contemplated. Needle 170 is formed from an electrically-conductive material of which at least distal end 176 is exposed. An insulating sleeve 180, or coating of material, surrounds the remaining portion of needle 170 that extends distally from engagement recess 116. With at least distal end 176 of needle 170 exposed, energy, e.g., RF energy, can be delivered from needle 170 to surrounding tissue to treat, e.g., ablate, tissue.

As mentioned above, an energy source, e.g., generator 20, is provided for providing power and/or control signals to needle electrode assembly 150 via line 22, one or more wires 123, and one or more pairs of contacts 122, 172. Further, a cooling fluid source 30 is provided for providing cooling fluid to needle electrode assembly 150. Cooling fluid source 30 provides cooling fluid, via line 32 (which includes both inflow and outflow lines), such that cooling fluid supplied by the cooling fluid source 30 may be circulated through hollow interior 174 of needle 170 to maintain needle electrode assembly 150 in a relatively cooled state during the application of energy to tissue. Cooperating valves 179, 129 of needle electrode assembly 150 and handle assembly 110, respectively, may be provided to facilitate the passage, e.g., inflow and outflow, of cooling fluid between cooling fluid source 30 and hollow interior 174 of needle 170, although other configurations are also contemplated. Circulation of the cooling fluid may be established through the use of a pump (not shown) or other suitable mechanism disposed within housing 112 of handle assembly 110, or the pump (not shown) may be externally disposed.

In operation, ablation device 100, lead by distal tip 178 of needle 170, is inserted into an operative site such that exposed distal end 176 of needle 170 of ablation device 100 is positioned adjacent to or within a target tissue to be treated, e.g., ablated. A return pad or return electrode (not shown) may, at this point or prior to, be operatively adhered to or connected to the patient. With exposed distal end 176 of needle 170 in position, energy, e.g., RF energy, is delivered from generator 20 to needle 170 and is conducted from exposed distal end 176 of needle 170 through the target tissue, ultimately to be collected by the return electrode (not shown). An effective amount of energy at an effective energy level and for an effective duration of time is delivered to tissue to achieve the desired result, e.g., to treat the target tissue. To this end, one or more control switches 130 may be provided on handle assembly 110 for controlling the supply of energy to needle 170, or, alternatively, the supply of energy may be automatically or manually controlled by generator 20.

Either prior to or simultaneously with the delivery of electrosurgical energy to needle 170, the cooling fluid provided by cooling fluid source 30 may be circulated through hollow interior 174 of needle 170 to withdraw heat from needle 170, thus maintaining needle 170 in a relatively cooled state during use. The delivery of cooling fluid to hollow interior 174 of needle 170 may likewise be controlled by one or more control switches 130 disposed on handle assembly 110, or via cooling fluid supply 30 itself.

At the completion of the procedure, needle electrode assembly 150 may be disengaged from handle assembly 110 and discarded, in those embodiments where needle electrode assembly 150 is configured as a single-use component or where needle electrode assembly 150 has reached its usage limit or maximum number of uses, or may be sterilized for re-use, in those embodiments where needle electrode assembly 150 has yet to reach its usage limit or maximum number of uses. Handle assembly 110 is configured as a reusable component and, thus, is sterilizable for re-use, although handle assembly 110 may also be configured as a disposable component.

Turning now to FIGS. 3A-3B, 4A-4B, 5A-5C, and 6, various different embodiments of ablation devices including needle electrode assemblies similar to needle electrode assembly 150 (FIGS. 1-2) and configured for releasable engagement with a handle assembly similar to handle assembly 110 (FIGS. 1-2), are described hereinbelow. Each of the ablation devices includes one or more single-use or limited use features for inhibiting re-use or limiting the use of the needle electrode assembly. Further, any of the ablation devices described hereinbelow may include any or all of the features of ablation device 100 (FIGS. 1-2), described above, or any of the other ablation devices described herein.

Figure 3A:
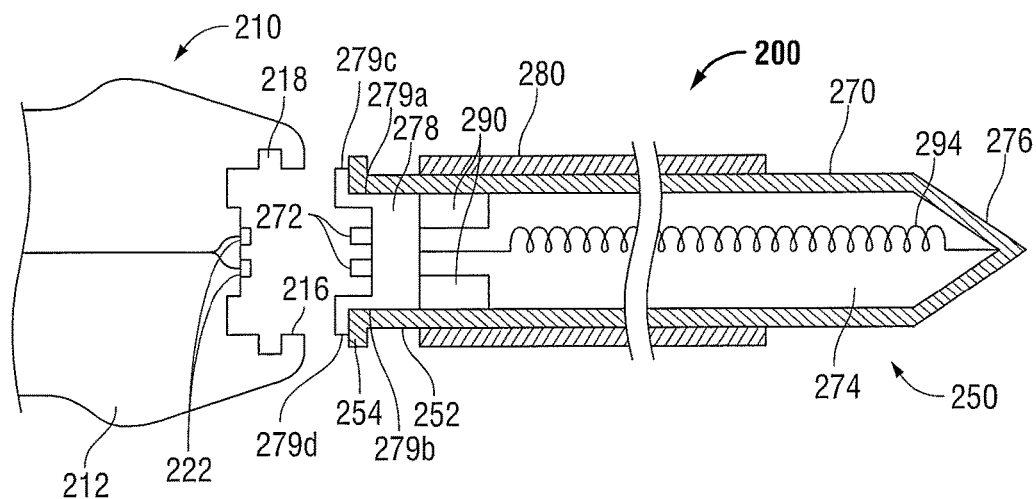
FIG. 3A is a longitudinal, cross-sectional view of an electrosurgical ablation device provided in accordance with the present disclosure wherein a needle electrode assembly of the electrosurgical ablation device is disposed in a usable condition and is disengaged from a handle assembly thereof.
Figure 3B:
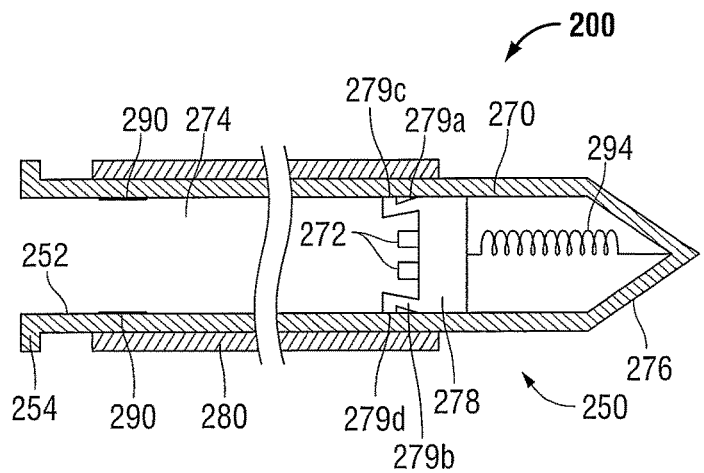
FIG. 3B is a longitudinal, cross-sectional view of the needle electrode assembly of FIG. 3A shown in a spent condition.

Referring to FIGS. 3A-3B, ablation device 200 is shown generally including a handle assembly 210 and a needle electrode assembly 250 releasably engagable with handle assembly 210. Handle assembly 210 includes a housing 212 defining an engagement recess 216 for releasably engaging proximal end 252 of needle electrode assembly 250 therein. More specifically, housing 212 includes a pair of notches 218 defined therein adjacent engagement recess 216 that are configured to receive complementary protrusions 254 extending outwardly from proximal end 252 of needle electrode assembly 250 for releasably engaging needle electrode assembly 250 therein. Housing 212 of handle assembly 210 is ultimately coupled to an energy source, e.g., generator 20 (FIG. 1), and a cooling fluid source, e.g., cooling fluid source 30 (FIG. 1), for supplying energy and cooling fluid, respectively, to needle electrode assembly 250.

One or more electrical contacts 222 of handle assembly 210 are configured to electrically couple to one or more corresponding electrical contacts 272 of needle electrode assembly 250 upon mechanical engagement of handle assembly 210 and needle electrode assembly 250 to one another, thereby establishing electrical communication between handle assembly 210 and needle electrode assembly 250 for transmitting power and/or control signals between generator 20 (FIG. 1), the control circuitry (not explicitly shown) of handle assembly 210, and needle electrode assembly 250. Cooperating valves, e.g., valves 129, 179 (FIG. 2), of handle assembly 250 and needle electrode assembly 250 may also be provided to permit passage, e.g., inflow and outflow, of cooling fluid between the cooling fluid source 30 (FIG. 1) and hollow interior 274 of needle 270 of needle electrode assembly 250.

Needle 270 of needle electrode assembly 250 is formed from an electrically-conductive material, defines a hollow interior 274, and includes an insulative sleeve (or coating) 280 disposed about a portion of the external surface of needle 270. Needle 270 of needle electrode assembly 250, as shown in FIGS. 3A-3B, further includes a platform 278 that supports contacts 272 thereon. First and second arms 279a, 279b, respectively, extend from platform 278 and each include an outwardly-extending finger 279c, 279d, respectively, disposed at the free end thereof that is configured for engagement (along with protrusions 254) within notches 218 defined within housing 212 to maintain contacts 222, 272 in electrical communication to one another when handle assembly 210 and needle electrode assembly 250 are mechanically engaged to one another. Any other suitable mechanism for retaining platform 278 at proximal end 252 of needle electrode assembly 250 such that contacts 222, 272 are maintained in electrical communication with one another during use may also be provided.

Platform 278 of needle electrode assembly 250 is initially supported by one or more support members 290 adhered, engaged, or otherwise secured to the inner surface of needle 270. Platform 278 is also coupled to distal end 276 of needle 270 via a biasing member 294, e.g., a spring. Support members 290, as will be described in greater detail below, may be formed from a dissolvable or dispersable material, a contractible material, a collapsible structure (e.g., a collapsible scaffold), a phase-change material, or any other suitable material, member, component, or assembly, that is configured to transition between a first state, wherein support members 290 retain platform 278 and, thus, contacts 272 at proximal end 252 of needle electrode assembly 250, and a second state, wherein support members 290 no longer support platform 278, thus permitting platform 278 to retract distally into hollow interior 274 of needle 270 under the bias of biasing member 294.

Support members 290 may be configured to transition from the first state to the second state upon contact with one or more fluids, e.g., cooling fluid; support members 290 may be temperature-sensitive, e.g., wherein support members 290 transition from the first state to the second state upon heating to a pre-determined temperature; support members 290 may be chemically-sensitive, e.g., wherein support members 290 transition from the first state to the second state upon contact with a particular chemical (or chemicals); support members 290 may be electrically-sensitive, e.g., wherein support members 290 transition from the first state to the second state upon application of electrical energy thereto; and/or support members 290 may otherwise be configured to selectively transition from the first state to the second state. Further, support members 290 may alternatively or additionally include time-sensitive features such that support members 290 are transitioned from the first state to the second state, for example, upon exposure to one or more fluids, a pre-determined temperature, etc., for a pre-determined amount of time. In fact, needle 270 may include any suitable material, member, component, or assembly disposed within hollow interior 274 thereof that is configured to transition, upon occurrence of a particular event (or events), from a first state, wherein support members 290 retain platform 278 and, thus, contacts 272 at proximal end 252 of needle electrode assembly 250, and a second state, wherein support members 290 no longer support platform 278, thus permitting platform 278 to retract distally into hollow interior 274 of needle 270 under the bias of biasing member 294.

The assembly and operation of ablation device 200 is described with reference to FIGS. 3A-3B. As shown in FIG. 3A, needle electrode assembly 250 is initially disposed in a usable condition and, accordingly, platform 278 is retained at proximal end 252 of needle electrode assembly 250 via support members 290 (with support members 290 disposed in the first state). With needle electrode assembly 250 disposed in this usable condition, in preparation for use, needle electrode assembly 250 is inserted into recess 216 of housing 212 of handle assembly 210 to releasably engage handle assembly 210 and needle electrode assembly 250 to one another. Upon engagement of handle assembly 210 and needle electrode assembly 250 to one another, since support members 290 retain platform 278 and contacts 272 at proximal end 252 of needle electrode assembly 250, electrical contacts 222, 272 are likewise coupled to one another to electrically couple handle assembly 210 and needle electrode assembly 250 to one another. Valves, e.g., valves 129, 179 (FIG. 2), of handle assembly 210 and needle electrode assembly 250 may also be coupled to one another upon engagement of handle assembly 210 and needle electrode assembly 250 to one another to permit the inflow/outflow of cooling fluid therebetween.

With needle electrode assembly 250 mechanically engaged and electrically coupled to handle assembly 210, ablation device 200 is ready for use. The use of ablation device 200 is similar to that of ablation device 100 (FIGS. 1-2) described above and, thus, will not be repeated here. After use, needle electrode assembly 250 is disengaged from handle assembly 210 and is discarded or sterilized for re-use. Handle assembly 210 is configured as a reusable component and, thus, is sterilized for re-use. Alternatively, handle assembly 210 may be configured as a disposable component.

As mentioned above, the circulation of cooling fluid through hollow interior 274 of needle 270, the supply of electrosurgical energy to needle 270, heat, chemicals, and/or any other suitable occurrence after a pre-determined number of uses, a pre-determined number of sterilizations, and/or a pre-determine usage time, transitions support members 290 of needle electrode assembly 250 from the first state, shown in FIG. 3A, to the second state, shown in FIG. 3B. Upon transitioning of support members 290 from the first state to the second state, support members 290 no longer support platform 278 at proximal end 252 of needle electrode assembly 250 and, thus, platform 278 is retracted distally into hollow interior 274 of needle 270 under the bias of biasing member 294. This corresponds to the spent condition of needle electrode assembly 250.

In embodiments where support members 290 are transitioned from the first state to the second state during use, e.g., while needle electrode assembly 250 is still engaged to handle assembly 210, the engagement of fingers 279c, 279d of platform 278 within notches 218 of housing 212 maintains platform 278 at proximal end 252 of needle electrode assembly 250 during use. Accordingly, contacts 222, 272 remain coupled to one another, thus maintaining electrical communication between handle assembly 210 and needle electrode assembly 250 during use. However, once needle electrode assembly 250 is disengaged from handle assembly 210 (or in embodiments wherein support members 290 are transitioned from the first state to the second state when needle electrode assembly 250 is disengaged from handle assembly 210, e.g., during sterilization), platform 278 is retracted distally into hollow interior 274 of needle 270 under the bias of biasing member 294.

Alternatively, in embodiments where contacts 222, 272 are used to identify and/or verify needle electrode assembly 250 upon engagement to handle assembly 210 (while additional contacts are utilized to supply energy to needle electrode assembly 250), contacts 222, 272 need only be coupled to one another during the engagement of needle electrode assembly 250 and handle assembly 210 to one another to verify that an acceptable needle electrode assembly 250 is engaged to handle assembly 210 and/or to identify needle electrode assembly 250. Thus, contacts 222, 272 need not be retained in electrical communication with one another throughout the use of ablation device 200 but, rather, are permitted to be retracted within hollow interior 274 of needle 270 immediately upon occurrence of the pre-determined event(s) and without effecting the operation of ablation device 200. Accordingly, in such embodiments, fingers 279c, 279d, need not be provided.

Referring now to FIG. 3B, upon subsequent attempted use of needle electrode assembly 250 with needle electrode assembly 250 disposed in the spent condition, needle electrode assembly 250 may be mechanically engaged to handle assembly 210, but is inhibited from being electrically coupled to handle assembly 210 since contacts 272 are retracted within hollow interior 274 of needle 270. As such, reuse of needle electrode assembly 250 is inhibited once contacts 272 are retracted, e.g., the supply of electrical energy to (or identification of) needle electrode assembly 250 is inhibited. More specifically, depending on the configuration of support members 290, e.g., depending on what event(s) effect transitioning of support members 290 to the second state, use of needle electrode assembly 250 may be subsequently inhibited after a single use, a pre-determined number of uses, or a pre-determined amount of use time.

Figure 4A:
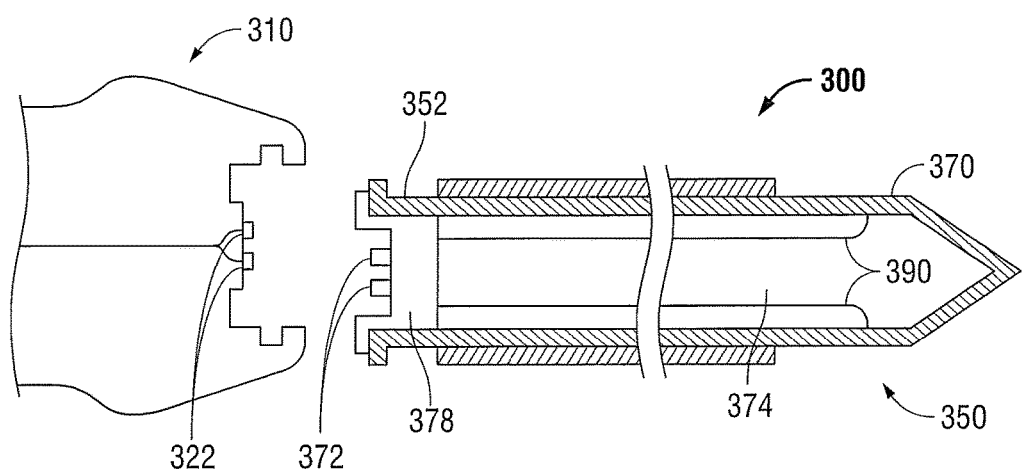
FIG. 4A is a longitudinal, cross-sectional view of an electrosurgical ablation device provided in accordance with the present disclosure wherein a needle electrode assembly of the electrosurgical ablation device is disposed in a usable condition and is disengaged from a handle assembly thereof.
Figure 4B:
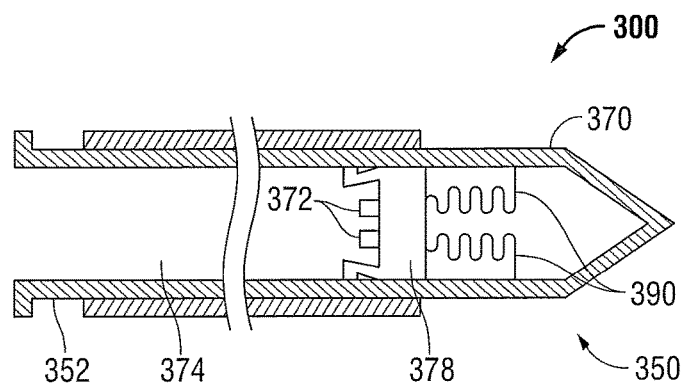
FIG. 4B is a longitudinal, cross-sectional view of the needle electrode assembly of FIG. 4A shown in a spent condition.

Turning now to FIGS. 4A-4B, another embodiment of an ablation device 300 provided in accordance with the present disclosure is shown generally including a handle assembly 310 and a needle electrode assembly 350 releasably engagable with handle assembly 310. Ablation device 300 is similar to ablation device 200 (FIGS. 3A-3B) and, thus, only the differences therebetween will be described in detail hereinbelow. More specifically, ablation device 300 differs from ablation device 200 (FIGS. 3A-3B) in that needle 370 of needle electrode assembly 350 does not include support members supporting platform 378 and a biasing member biasing platform 378 distally. Rather, platform 378 is initially retained at proximal end 352 of needle electrode assembly 350 via one or more retention elements 390.

Retention elements 390 may be formed at least partially from a shape memory material, or any other suitable material configured to transition between a first state, wherein retention elements 390 are extended, thus retaining platform 378 at proximal end 352 of needle electrode assembly 350 to facilitate electrical coupling of contacts 322, 372 to one another, and a second state, wherein retention elements 390 are contracted, thereby retracting platform 378 and contacts 372 distally into hollow interior 374 of needle 370 to inhibit electrical coupling of needle electrode assembly 350 and handle assembly 310 to one another. Similarly as described above with respect to support members 290 (FIG. 3A), retention elements 390 may be configure to transition between the first and second states upon contact with one or more fluids, may be temperature-sensitive, chemically-sensitive, electrically-sensitive, and/or otherwise configured to selectively transition from the first state to the second state upon occurrence of any suitable event. Retention elements 390 may additionally or alternatively be time-dependent, similarly as described above.

Figure 5A:
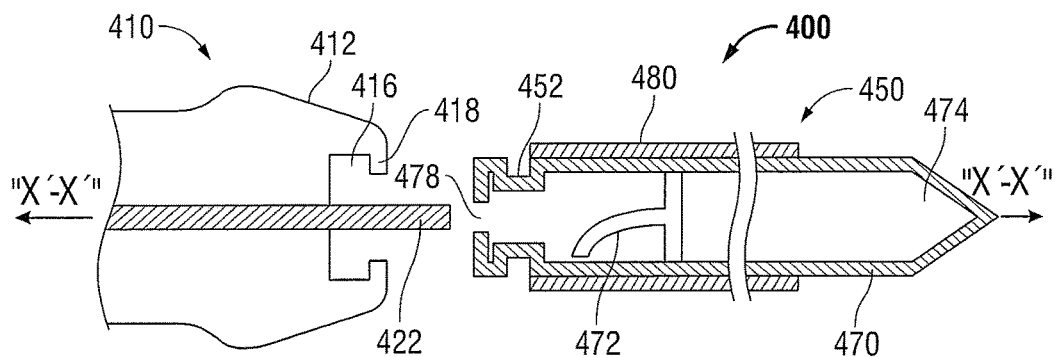
FIG. 5A is a longitudinal, cross-sectional view of another electrosurgical ablation system provided in accordance with the present disclosure wherein a needle electrode assembly is disengaged from a handle assembly thereof.
Figure 5B:
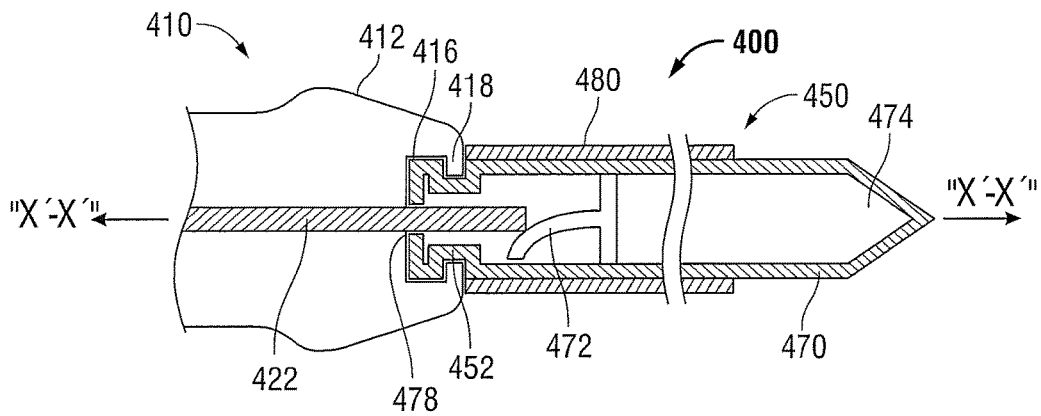
FIG. 5B is a longitudinal, cross-sectional view of the electrosurgical ablation system of FIG. 5A wherein the needle electrode assembly is engaged to the handle assembly.
Figure 5C:
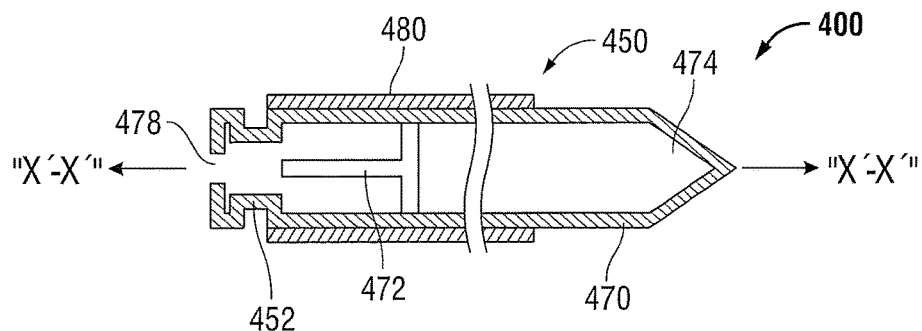
FIG. 5C is a longitudinal, cross-sectional view of the needle electrode assembly of FIGS. 5A-5B shown in a spent condition.

Turning now to FIGS. 5A-5C, another embodiment of an ablation device provided in accordance with the present disclosure is shown generally identified by reference numeral 400. Ablation device 400 includes a handle assembly 410 and a needle electrode assembly 450 that defines a longitudinal axis "X'-X'" and is releasably engagable with handle assembly 410. Handle assembly 410 includes a housing 412 defining an engagement recess 416 for releasably engaging proximal end 452 of needle electrode assembly 450 therein. More specifically, housing 412 includes a pair of tabs 418 extending into engagement recess 416 that are configured to releasably retain proximal end 452 of needle electrode assembly 450 within engagement recess 416. Other releasable engagement mechanisms, e.g., snap-fit engagements, threaded-engagements, friction-fit engagements, etc., are also contemplated. Housing 412 of handle assembly 410 is configured to couple to an energy source, e.g., generator 20 (FIG. 1), and a cooling fluid source, e.g., cooling fluid source 30 (FIG. 1), respectively, for supplying energy and cooling fluid, respectively, to needle electrode assembly 450.

Continuing with reference to FIGS. 5A-5C, handle assembly 410 further includes a first contact pin 422 extending distally from housing 412 into engagement recess 416. First contact pin 422 is configured to electrically couple to a corresponding, second contact pin 472 disposed within hollow interior 474 of needle 470 of needle electrode assembly 450 upon mechanical engagement of handle assembly 410 and needle electrode assembly 450 to one another, thereby establishing electrical communication between handle assembly 410 and needle electrode assembly 450. More specifically, contact pins 422, 472, may be configured for establishing a conductive path for transmission of energy between generator 20 (FIG. 1) and needle electrode assembly 450 and/or for identifying or verifying the needle electrode assembly engaged with handle assembly 410. One or more contacts, e.g., contacts 122, 172, (FIG. 2), disposed on handle assembly 410 and needle electrode assembly 450 may additionally or alternatively be provided for similar purposes.

Needle 470 of needle electrode assembly 450 is formed from an electrically-conductive material, defines a hollow interior 474, and includes an insulative sleeve (or coating) 480 disposed about a portion of the external surface of needle 470. Needle 470 of needle electrode assembly 450 defines a proximal end 452 that is configured for engagement within engagement recess 416 defined within housing 412 of handle assembly 410 and an aperture 478 extending through proximal end 452 thereof in general alignment with longitudinal axis "X'-X'." First contact pin 422 is configured for insertion into hollow interior 474 of needle 470 to permit engagement of needle electrode assembly 450 and handle assembly 410 to one another. Needle electrode assembly 450 further includes a second contact pin 472 disposed within hollow interior 474 of needle 470 and extending towards proximal end 452 thereof. Second contact pin 472 is initially disposed in a bent configuration (FIGS. 5A-5B), wherein a portion of contact pin 472 is bent, or displaced off of longitudinal axis "X'-X'," thus permitting insertion of first contact pin 422 of handle assembly 410 through aperture 478 and at least partially into hollow interior 474 of needle 470. Second contact pin 472 is movable from this bent configuration to an aligned configuration (FIG. 5C), wherein second contact pin 472 is substantially aligned with longitudinal axis "X'-X'" and aperture 478, thus inhibiting substantial insertion of first contact pin 422 through aperture 478 and into hollow interior 474 of needle 470. Second contact pin 472 of needle electrode assembly 450 may be formed from a ferromagnetic material, a shape-memory material, or any other suitable material configured to transition from the bent configuration to the aligned configuration upon occurrence of a pre-determined event(s), as will be described in greater detail below.

The assembly and operation of ablation device 400 is described with reference to FIGS. 5A-5C. As shown in FIG. 5A, needle electrode assembly 450 is initially disposed in an unused condition wherein second contact pin 472 is disposed in the bent configuration. In preparation for use, needle electrode assembly 450 is inserted into recess 416 of housing 412 of handle assembly 410 to releasably engage handle assembly 410 and needle electrode assembly 450 to one another. Engagement of handle assembly 410 and needle electrode assembly 450 is permitted at this point since second contact pin 472 is disposed in the bent configuration, thus permitting first contact pin 422 to be inserted through aperture 478 needle electrode assembly 450 and into hollow interior 474 of needle 470 sufficiently so as to permit engagement of handle assembly 410 and needle electrode assembly 450 to one another.

In the engaged position, as shown in FIG. 5B, first contact pin 422 extends through aperture 478 and into contact with the bent second contact pin 472, establishing electrical communication therebetween, e.g., for identification/verification of needle electrode assembly 450, transmitting energy to needle electrode assembly 450, and/or transmitting control signals between needle electrode assembly 450, handle assembly 410, and generator 20 (FIG. 1). Valves, e.g., valves 129, 179 (FIG. 2), of handle assembly 410 and needle electrode assembly 450 may also be coupled to one another upon engagement of handle assembly 410 and needle electrode assembly 450 to one another to permit the inflow/outflow of cooling fluid therebetween.

With needle electrode assembly 450 mechanically engaged and electrically coupled to handle assembly 410, ablation device 400 is ready for use. The use of ablation device 400 is similar to that of ablation device 100 (FIGS. 1-2) described above and, thus, will not be repeated here. After use, needle electrode assembly 450 is disengaged from handle assembly 410 and is discarded or sterilized for re-use. Handle assembly 410 is configured as a reusable component and, thus, is also sterilized for re-use, although handle assembly 410 may alternatively be configured as a disposable component.

With reference to FIG. 5C, in conjunction with FIGS. 5A-5B, as mentioned above, second contact pin 472 is transitionable from the initial, bent configuration (FIGS. 5A-5B) to the aligned configuration (FIG. 5C) upon occurrence of a pre-determined event (or events). For example, in embodiments wherein second contact pin 472 is at least partially formed from a ferromagnetic material, second contact pin 472 may be configured such that second contact pin 472 is initially retained in the bent condition, wherein second contact pin 472 is bent towards needle 470 due to magnetic attraction therebetween. Upon supply of electrosurgical energy to needle 470 during use (or the heat applied thereto during sterilization), second contact pin 472 is heated to or above its Curie point, thereby changing, e.g., eliminating, the magnetic field and allowing second contact pin 472 to return, in the absence of magnetic bias, to the aligned condition, as shown in FIG. 5C. When second contact pin 472 is disposed in the aligned position, needle electrode assembly 450 is correspondingly disposed in a spent condition.

Referring now to FIG. 5C, upon subsequent attempted use of needle electrode assembly 450 with needle electrode assembly 450 disposed in the spent condition, re-engagement of handle assembly 410 and needle electrode assembly 450 to one another is mechanically inhibited due to the disposition of second contact pin 472 in alignment with aperture 478. That is, second contact pin 472 inhibits first contact pin 422 from being sufficiently inserted into hollow interior 474 of needle 470, thus inhibiting proximal end 452 of needle electrode assembly 450 from being inserted sufficiently into engagement recess 416 of housing 412 so as to engage needle electrode assembly 450 and handle assembly 410 to one another. As such, repeated use of needle electrode assembly 450 is inhibited.

Figure 6:
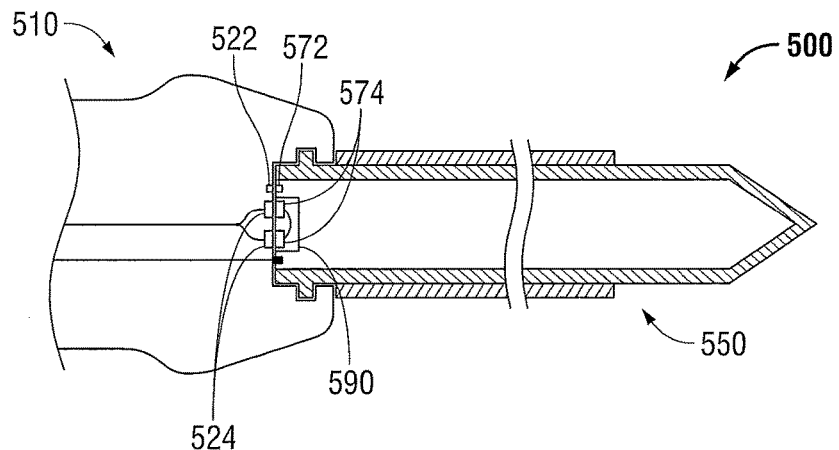
FIG. 6 is a longitudinal, cross-sectional view of another electrosurgical ablation system provided in accordance with the present disclosure showing a needle electrode assembly engaged to a handle assembly thereof.

Turning now to FIG. 6, another embodiment of an ablation device provided in accordance with the present disclosure is shown generally identified by reference numeral 500. Ablation device 500 is similar to those ablation devices described above and generally includes a handle assembly 510 and a needle electrode assembly 550 releasably engagable with handle assembly 510. Handle assembly 510 includes one or more first contacts 522 configured to electrically couple to corresponding first contacts 572 of needle electrode assembly 550 such that power and/or control signals may be transmitted between generator 20 (FIG. 1) and needle electrode assembly 550 via the electrically-coupled first contacts 522, 572.

Handle assembly 510 further includes one or more second contacts 524 configured to electrically couple to corresponding second contacts 574 of needle electrode assembly 550 upon engagement of handle assembly 510 and needle electrode assembly 550 to one another to identify and/or verify needle electrode assembly 550. Second contacts 574 of needle electrode assembly 550 are coupled to one another via a destructive circuit or cell 590, e.g., a galvanic cell, that is configured to self-destruct, e.g., corrode, after initial coupling of second contacts 524, 574, of handle assembly 510 and needle electrode assembly 550, respectively, thereby rendering second contacts 574 of needle electrode assembly 550 inoperable. Accordingly, upon subsequent engagement of handle assembly 510 and needle electrode assembly 550 to one another, with second contacts 574 of needle electrode assembly 550 no longer operable, identification and/or verification of needle electrode assembly 550 is not established and, as a result, needle electrode assembly 550 is rejected by handle assembly 510 and/or generator 20 (FIG. 1). Thus, the destructive cell 590, e.g., the galvanic cell, inhibits reuse of needle electrode assembly 550.

Figure 7A:
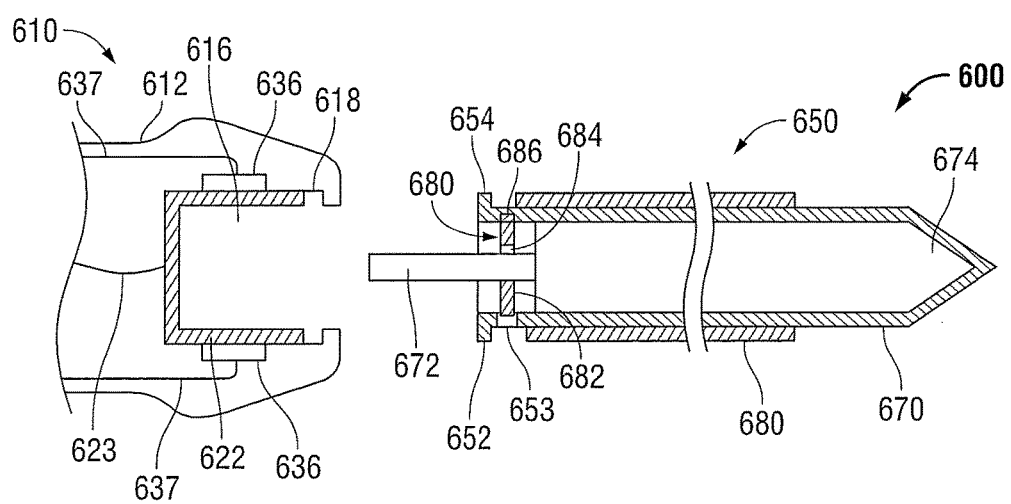
FIG. 7A is a longitudinal, cross-sectional view of another electrosurgical ablation system provided in accordance with the present disclosure wherein a needle electrode assembly is disengaged from a handle assembly thereof.
Figure 7B:
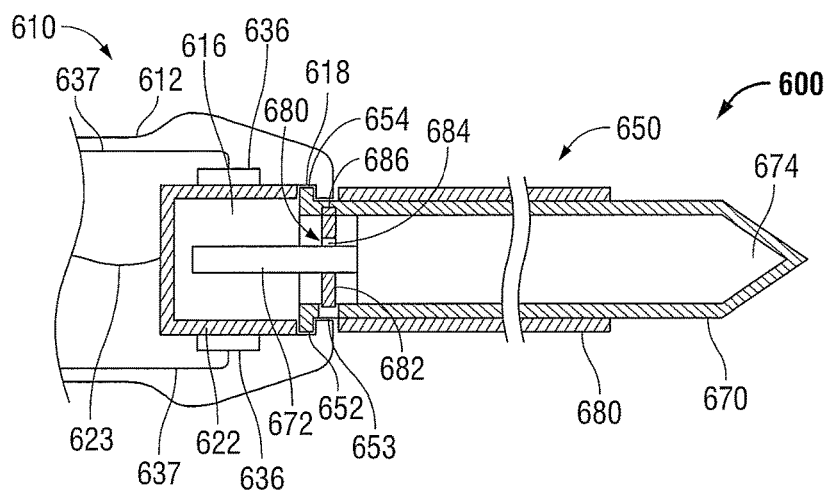
FIG. 7B is a longitudinal, cross-sectional view of the electrosurgical ablation system of FIG. 7A showing the needle electrode assembly mechanically engaged to the handle assembly.
Figure 7C:
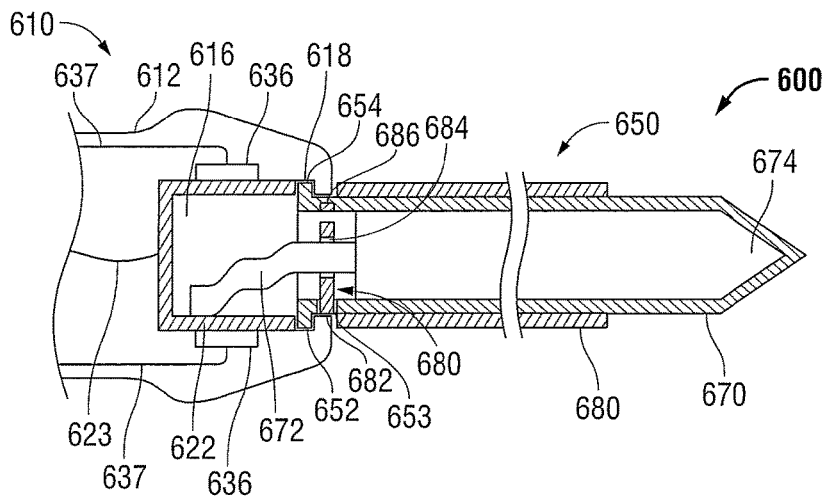
FIG. 7C is a longitudinal, cross-sectional view of the electrosurgical ablation system of FIG. 7A showing the needle electrode assembly mechanically engaged and electrically coupled to the handle assembly.

Turning now to FIGS. 7A-7C, another embodiment of an ablation device provided in accordance with the present disclosure is shown generally identified by reference numeral 600. Ablation device 600 generally includes a handle assembly 610 and a needle electrode assembly 650 releasably engagable with handle assembly 610. Needle electrode assembly 650 of ablation device 600 is configured as a disposable component, e.g., needle electrode assembly 650 is disposable after a single use, a predetermined number of uses, or a predetermined amount of use time. Accordingly, needle electrode assembly 650 may include any of the limiting-reuse features of those ablation devices described above or, as will be described below, may incorporate a lockout mechanism 680 configured to inhibit reuse of needle electrode assembly 650. Handle assembly 610 of ablation device 600, on the other hand, is configured as a reusable component. Handle assembly 610, as will be described in greater detail below, is configured such that wear on the electrical contact(s) of handle assembly 610 for electrically coupling to needle electrode assembly 650 is substantially reduced. As a result, the life of handle assembly 610 can be extended without the concern of wearing due to repeated engagement/disengagement of needle electrode assembly 650 therewith.

Continuing with reference to FIGS. 7A-7C, handle assembly 610 of ablation device 600 includes a housing 612 defining an engagement recess 616 therein that is configured to receive proximal end 652 of needle electrode assembly 650 for releasably engaging needle electrode assembly 650 and handle assembly 610 to one another. More specifically, engagement recess 616 of housing 612 defines one or more notches 618 therein that are configured to engage protrusions 654 extending outwardly from proximal end 652 of needle electrode assembly 650 to releasably mechanically engage needle electrode assembly 650 and handle assembly 610 to one another. Other releasable engagement mechanisms, e.g., snap-fit engagements, threaded-engagements, friction-fit engagements, etc., are also contemplated. An electrical contact 622 extends about, e.g., lines, at least a portion of the inner surface of housing 612 that defines recess 616. Contact 622 is coupled to wires 623 that extend through housing 612 of handle assembly 610, ultimately coupling to a source of energy, e.g., generator 20 (FIG. 1). Handle assembly 610 may further be configured to couple to a cooling fluid source, e.g., cooling fluid source 30 (FIG. 1) for supplying cooling fluid to needle electrode assembly 650, similarly as described above. Housing 612 of handle assembly 610 of ablation device 600 further includes one or more activation members 636 disposed adjacent recess 616 and coupled to generator 20 (FIG. 1), or other suitable energy source, via wire(s) 637. The importance of activation members 636 will become more apparent below.

Needle electrode assembly 650 is similar to those described above and includes an electrically-conductive needle 670 defining a hollow interior 674, and an insulative sleeve (or coating) 680 disposed about a portion of the external surface of needle 670. Needle electrode assembly 650 further includes an electrical contact pin 672 extending proximally therefrom that is configured to couple to contact 622 of handle assembly 610 for identifying or verifying the identification of needle electrode assembly 650. One or more contacts, e.g., contacts 122, 172, (FIG. 2), disposed on handle assembly 610 and needle electrode assembly 650 may additionally or alternatively be provided for transmission of energy between generator 20 (FIG. 1) and needle electrode assembly 650. In either configuration, at least a portion of electrical contact pin 672 is formed from a transitionable material, e.g., a shape-memory material, or a ferromagnetic (or anti-ferromagnetic) material, such that, upon heating of contact pin 672 or upon introduction of an electromagnetic field to contact pin 672, contact pin 672 is transitioned between a first condition, as shown in FIGS. 7A and 7B, wherein contact pin 672 defines a generally linear configuration, and a second condition, as shown in FIG. 7C, wherein contact pin 672 is deflected to contact electrical contact surface 622 of handle assembly 610, thereby establishing electrical communication therebetween.

Needle electrode assembly 650, as mentioned above, may further include a lockout mechanism 680 disposed at the proximal end of needle electrode assembly 650 and configured to inhibit reengagement of needle electrode assembly 650 and handle assembly 610 after use. Lockout mechanism 680 includes a lockout member 682 disposed about contact pin 672 and defining an aperture 684 configured to permit passage of contact pin 672 therethrough. Lockout member 682 is formed from a transitionable material, e.g., a shape-memory material, or a ferromagnetic (or anti-ferromagnetic) material, and/or is coupled to needle electrode assembly 650 via a transitionable material, e.g., engagement member 686, such that, as will be described in greater detail below, lockout member 682 is movable from an initial position, wherein lockout member 682 does not protrude outwardly from needle electrode assembly 650, to an extended position, wherein, upon heating of lockout member 682 via activation members 636 or upon introduction of an electromagnetic field to lockout member 682 via activation members 636 (and/or via heating or introduction of an electromagnetic field to engagement member 686), lockout member 682 is biased to extend transversely through aperture 653 of needle electrode assembly 650 and outwardly from needle electrode assembly 650 to mechanically inhibit re-engagement of needle electrode assembly 650 to handle assembly 610.

Referring still to FIGS. 7A-7C, the assembly of needle electrode assembly 650 to handle assembly 610 is described. Initially, as shown in FIG. 7A, with contact pin 672 disposed in the first condition, and with lockout member 682 disposed in the initial position, proximal end 652 of needle electrode assembly 650 may be inserted into recess 616 of handle assembly 610 to releasably engage needle electrode assembly 650 therein, e.g., via the engagement of protrusions 654 within notches 618.

With reference to FIG. 7B, although needle electrode assembly 650 and handle assembly 610 are mechanically engaged to one another at this point, needle electrode assembly 650 and handle assembly 610 are not electrically coupled to one another. That is, with contact pin 672 disposed in the first condition, contact pin 672 extends into recess 616 in general spaced-apart relation relative to contact 622 of handle assembly 610. Likewise, at this point, lockout member 682 remains disposed in the initial position. As such, if needle electrode assembly 650 is engaged to handle assembly 610, but is not activated for use, lockout mechanism 680 is not triggered and, thus, disengagement and subsequent reengagement of needle electrode assembly 650 and handle assembly 610 is permitted.

Turning to FIG. 7C, in order to electrically couple needle electrode assembly 650 and handle assembly 610 to one another, activation members 636 are activated to heat or apply an electromagnetic field to contact pin 672. More specifically, in embodiments where contact pin 672 is formed from a shape memory material, activation members 636 function as heaters to sufficiently heat contact pin 672 so as to transform contact pin 672 from its austenite shape, e.g., the first condition, to its martensite shape, e.g., the second condition, thereby electrically coupling contact 672 to contact 622 of handle assembly 610. In embodiments wherein contact pin 672 is formed at least partially from a ferromagnetic material, activation members 636 function as electromagnets to apply an electromagnetic field to contact pin 672 such that contact pin 672 is deflected to the second condition, shown in FIG. 7C, wherein contact pin 672 is electrically coupled to contact 622 of handle assembly 610. With contacts 622, 672 coupled to one another, electrical communication is established between needle electrode assembly 650 and handle assembly 610, thus permitting use of ablation device 600, similarly as described above.

Simultaneously or near-simultaneously with the transition of contact pin 672 from the first condition to the second condition to electrically couple contact 672 of needle electrode assembly 650 to contact 622 of handle assembly 610, activation members 636 transition lockout member 682 and/or engagement member 686, e.g., via heating or applying an electromagnetic field thereto, such that lockout member 682 is urged from the initial position towards the extended position. However, at this point, the engagement of needle electrode assembly 650 within handle assembly 610 inhibits full extension of lockout member 682 to the extended position. Rather, lockout member 682 is not fully moved to the extended position until needle electrode assembly 650 is disengaged from handle assembly 610. Upon disengagement, lockout member 682 is biased to extend transversely through aperture 653 of needle electrode assembly 650 and outwardly from needle electrode assembly 650, e.g., the fully extended position, to mechanically inhibit re-engagement of needle electrode assembly 650 to handle assembly 610.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
a reusable component including a reusable handle assembly and a first electrical contact; and
a limited-use component releasably engagable with the reusable component, the limited-use component including a limited-use needle electrode assembly configured to mechanically engage the reusable handle assembly and a second electrical contact configured to electrically couple to the first electrical contact to establish electrical communication between the reusable component and the limited-use component, the second electrical contact movable relative to the limited-use needle electrode assembly from a first position, wherein the second electrical contact is disposed at a proximal end portion of the limited-use needle electrode assembly to facilitate direct contact with the first electrical contact upon mechanical engagement of the limited-use needle electrode assembly of the limited-use component and the reusable handle assembly of the reusable component, thereby enabling electrical communication between the reusable component and the limited-use component, to a second position, wherein the second electrical contact is retracted into the limited-use needle electrode assembly to inhibit direct contact with the first electrical contact upon mechanical engagement of the limited-use needle electrode assembly of the limited-use component and the reusable handle assembly of the reusable component, thereby inhibiting electrical communication between the reusable component and the limited-use component.

2. The surgical instrument according to claim 1, wherein second electrical contact is coupled to a biasing member and is supported via a support member, the support member configured to transition from a first condition, wherein the support member retains the second electrical contact in the first position against the bias of the biasing member, and a second condition, wherein the support member no longer supports the second electrical contact, thereby permitting the second electrical contact to move to the second position under the bias of the biasing member.

3. The surgical instrument according to claim 2, wherein the support member is transitioned from the first condition to the second condition upon at least one of: application of a fluid thereto, heating to a pre-determined temperature, application of electrical energy thereto, and application of chemicals thereto.

4. The surgical instrument according to claim 2, wherein the support member is formed from at least one of: a dissolvable material, a phase-change material, and a collapsible scaffold.

5. The surgical instrument according to claim 1, wherein the second electrical contact is supported by a retention element, the retention element transitionable from a first condition, wherein the retention element retains the second electrical contact in the first position, and a second condition, wherein the retention element effects movement of the second electrical contact to the second position.

6. The surgical instrument according to claim 5, wherein the retention element is transitioned from the first condition to the second condition upon at least one of: application of a fluid thereto, heating to a pre-determined temperature, application of electrical energy thereto, and application of chemicals thereto.

7. The surgical instrument according to claim 1, wherein electrical communication between the first and second electrical contacts is configured for at least one of: transmitting electrical energy to the reusable component and identifying the reusable component.

* * * * *